US012702364B2

(12) United States Patent
Zhao et al.

(10) Patent No.: US 12,702,364 B2
(45) Date of Patent: Aug. 11, 2026

(54) MEDICAL IMAGE PROCESSING METHOD, APPARATUS, AND SYSTEM

(71) Applicant: GE Precision Healthcare LLC, Waukesha, WI (US)

(72) Inventors: Bingjie Zhao, Beijing (CN); Jingting Li, Beijing (CN); Xueli Wang, Beijing (CN); Tiegong Zheng, Beijing (CN)

(73) Assignee: GE Precision Healthcare LLC, Waukesha, WI (US)

( * ) Notice: Subject to any disclaimer, the term of this patent is extended or adjusted under 35 U.S.C. 154(b) by 396 days.

(21) Appl. No.: 18/468,534

(22) Filed: Sep. 15, 2023

(65) Prior Publication Data

US 2024/0090863 A1 Mar. 21, 2024

(30) Foreign Application Priority Data

Sep. 19, 2022 (CN) ........................ 202211136541.8

(51) Int. Cl.

| | |
|---|---|
| ***A61B 6/46*** | (2024.01) |
| ***A61B 6/00*** | (2006.01) |
| ***A61B 6/03*** | (2006.01) |
| ***G06T 12/10*** | (2026.01) |

(52) U.S. Cl.

CPC .............. *A61B 6/032* (2013.01); *A61B 6/465* (2013.01); *A61B 6/469* (2013.01); *A61B 6/488* (2013.01); *A61B 6/5205* (2013.01); *A61B 6/5294* (2013.01); *A61B 6/545* (2013.01); *G06T 12/10* (2026.01); *G06T 2210/41* (2013.01); *G06T 2211/441* (2023.08)

(58) Field of Classification Search

None

See application file for complete search history.

(56) References Cited

U.S. PATENT DOCUMENTS

| | | | | |
|---|---|---|---|---|
| 7,602,880 | B2 * | 10/2009 | Hirokawa | A61B 6/032 378/108 |
| 8,744,039 | B2 * | 6/2014 | Hirokawa | A61B 6/032 378/108 |
| 9,254,107 | B2 * | 2/2016 | Sugaya | A61B 6/405 |
| 9,317,580 | B2 | 4/2016 | Cohen-Solal | |
| 9,471,987 | B2 * | 10/2016 | Harder | G06V 10/141 |
| 10,638,993 | B2 * | 5/2020 | Yun | A61B 6/466 |
| 11,955,228 | B2 * | 4/2024 | Thibault | G16H 50/70 |
| 12,002,204 | B2 * | 6/2024 | Wang | G06T 7/0012 |
| 12,067,715 | B2 * | 8/2024 | Wang | A61B 6/488 |
| 12,354,260 | B2 * | 7/2025 | Suehling | G06T 7/0012 |
| 2009/0046833 | A1 * | 2/2009 | Hirokawa | A61B 6/463 378/108 |

(Continued)

*Primary Examiner* — Thomas R Artman

(57) ABSTRACT

Provided in embodiments of the present application are a medical image processing method, apparatus, and system. The medical image processing apparatus includes an acquisition unit, which acquires a first scout image obtained after a scout scan is performed on a subject to be examined, a first determination unit, which determines, according to a preset correspondence between a scout image and a section image, a predicted section image corresponding to a first region of interest in the first scout image, and a display unit, which displays in real time an updated predicted section image and scanning parameters corresponding to the updated predicted section image.

15 Claims, 7 Drawing Sheets

(56) References Cited

U.S. PATENT DOCUMENTS

| | | | | |
|---|---|---|---|---|
| 2011/0091008 | A1* | 4/2011 | Hirokawa | A61B 6/5217<br>378/4 |
| 2013/0156151 | A1* | 6/2013 | Sugaya | A61B 6/544<br>378/16 |
| 2013/0311472 | A1* | 11/2013 | Cohen-Solal | G16H 30/20<br>707/737 |
| 2015/0043774 | A1* | 2/2015 | Harder | G06V 10/141<br>382/128 |
| 2017/0143292 | A1* | 5/2017 | Yun | A61B 6/032 |
| 2023/0070656 | A1* | 3/2023 | Suehling | G16H 50/20 |
| 2023/0080631 | A1* | 3/2023 | Wang | A61B 6/545<br>382/131 |
| 2023/0081601 | A1* | 3/2023 | Wang | A61B 6/488<br>378/96 |
| 2023/0187054 | A1* | 6/2023 | Thibault | G06T 17/00 |
| 2024/0074722 | A1* | 3/2024 | Li | A61B 6/545 |
| 2024/0090863 | A1* | 3/2024 | Zhao | A61B 6/5205 |

* cited by examiner

MEDICAL IMAGE PROCESSING METHOD, APPARATUS, AND SYSTEM

CROSS-REFERENCE TO RELATED APPLICATIONS

This application claims priority to Chinese Application No. 202211136541.8, filed on Sep. 19, 2022, the disclosure of which is incorporated herein by reference in its entirety.

TECHNICAL FIELD

Embodiments of the present application relate to the technical field of medical devices, and in particular to a medical image processing method, apparatus, and system.

BACKGROUND

During the scanning process of computed tomography (CT), first, a scanning protocol needs to be selected according to clinical needs and a scout image is obtained, and then diagnostic CT scanning parameters are set, and a formal diagnostic scan is started, a detector is used to acquire data of X-rays passing through a subject to be examined, and then the acquired X-ray data is processed to obtain projection data. The projection data may be used to reconstruct a CT image. Complete projection data can be used to reconstruct an accurate CT image for diagnosis.

It should be noted that the above introduction of the background is only set forth to help clearly and completely describe the technical solutions of the present application, and to facilitate the understanding of those skilled in the art.

SUMMARY

Provided in embodiments of the present application are a medical image processing method, apparatus and system.

According to an aspect of the embodiments of the present application, a medical image processing method is provided. The method includes acquiring a first scout image obtained after a scout scan is performed on a subject to be examined, determining, according to a preset correspondence between a scout image and a section image, a predicted section image corresponding to a first region of interest in the first scout image, and displaying the predicted section image and scanning parameters corresponding to the predicted section image.

According to an aspect of the embodiments of the present application, a medical image processing apparatus is provided. The apparatus includes an acquisition unit, which acquires a first scout image obtained after a scout scan is performed on a subject to be examined, a first determination unit, which determines, according to a preset correspondence between a scout image and a section image, a predicted section image corresponding to a first region of interest in the first scout image, and a display unit, which displays the predicted section image and scanning parameters corresponding to the predicted section image.

According to an aspect of the embodiments of the present application, a medical image processing system is provided. The medical image processing system includes a scan device, configured to perform a scout scan on a subject to be examined so as to obtain a first scout image, a processor, which determines, according to a preset correspondence between a scout image and a section image, a predicted section image corresponding to a first region of interest in the first scout image, and a display, which displays the predicted section image and scanning parameters corresponding to the predicted section image.

According to an aspect of the embodiments of the present application, a computer device is provided, and the medical image processing apparatus of the previous aspect may be implemented with the computer device.

One of the benefits of the embodiments of the present application is that a predicted section image corresponding to a first region of interest in a first scout image obtained by a scout scan is determined according to a preset correspondence between a scout image and a section image, and the predicted section image and scanning parameters corresponding to the predicted section image are displayed. Therefore, an operator can intuitively view the predicted section image and the scanning parameters corresponding to the predicted section image without a formal diagnostic scan, which helps the operator to confirm a scan range, select suitable scanning parameters, and evaluate the image quality.

With reference to the following description and drawings, specific implementations of the embodiments of the present application are disclosed in detail, and the means by which the principles of the embodiments of the present application can be employed are illustrated. It should be understood that the embodiments of the present application are not therefore limited in scope. Within the scope of the spirit and clauses of the appended claims, the embodiments of the present application comprise many variations, modifications, and equivalents.

BRIEF DESCRIPTION OF THE DRAWINGS

The included drawings are used to provide further understanding of the embodiments of the present application, which constitute a part of the description and are used to illustrate embodiments of the present application and explain the principles of the present application together with textual description. Evidently, the drawings in the following description are merely some embodiments of the present application, and a person of ordinary skill in the art may obtain other embodiments according to the drawings without involving inventive skill. In the drawings.

DETAILED DESCRIPTION

Figure 1:
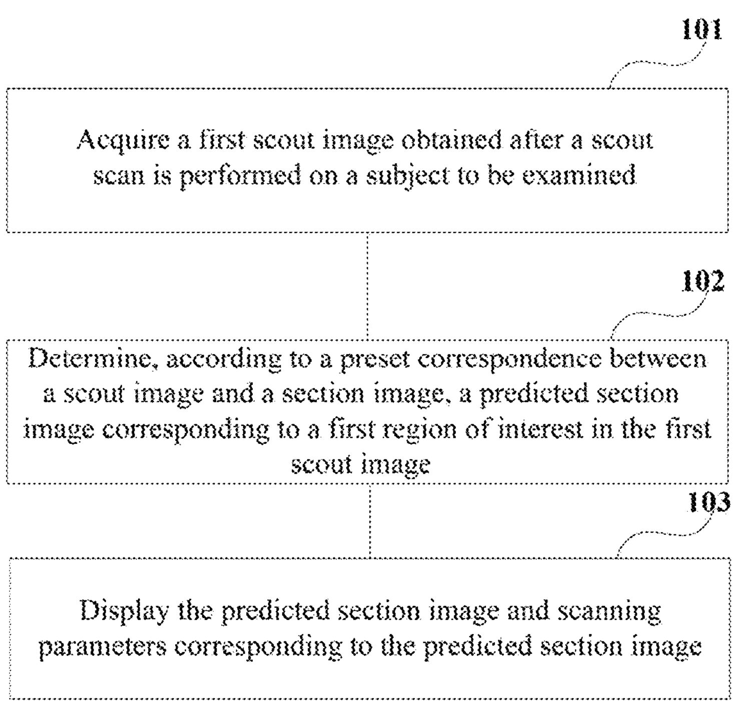
FIG. 1 is a schematic diagram of a medical image processing method of embodiments of the present application.

The foregoing and other features of the embodiments of the present application will become apparent from the following description and with reference to the drawings. In the description and drawings, specific embodiments of the present application are disclosed in detail, and part of the implementations in which the principles of the embodiments of the present application may be employed therein are indicated. It should be understood that the present application is not limited to the described implementations. On the contrary, the embodiments of the present application include all modifications, variations, and equivalents which fall within the scope of the appended claims.

In the embodiments of the present application, the terms "first" and "second" and so on are used to distinguish different elements from one another by their title, but do not represent the spatial arrangement, temporal order, or the like of the elements, and the elements should not be limited by said terms. The term "and/or" includes any one of and all combinations of one or more associated listed terms. The terms "comprise", "include", "have", etc., refer to the presence of stated features, elements, components, or assemblies, but do not exclude the presence or addition of one or more other features, elements, components, or assemblies. The terms "pixel" and "voxel" may be used interchangeably.

In the embodiments of the present application, the singular forms "a", "the", and the like include plural forms, and should be broadly understood as "a type of" or "a class of" rather than limited to the meaning of "one". In addition, the term "said" should be understood as including both the singular and plural forms, unless otherwise clearly specified in the context. In addition, the term "according to" should be construed as "at least in part according to . . . ", and the term "on the basis of" should be construed as "at least in part on the basis of . . . ", unless otherwise specified in the context.

The features described and/or illustrated for one embodiment may be used in one or more other embodiments in an identical or similar manner, combined with features in other embodiments, or replace features in other embodiments. The term "include/comprise" when used herein refers to the presence of features, integrated components, steps, or assemblies, but does not exclude the presence or addition of one or more other features, integrated components, steps, or assemblies.

The apparatus described herein for obtaining medical imaging data may be suitable for a variety of medical imaging modalities, including but not limited to Computed Tomography (CT) apparatuses, Magnetic Resonance Imaging (MRI) apparatuses, Positron Emission Tomography (PET) apparatuses, Single Photon Emission Computed Tomography (SPECT) apparatuses, PET/CT, PET/MR, or any other appropriate medical imaging apparatuses.

A system for obtaining medical images may include the aforementioned medical imaging apparatus, and may also include a separate computer device connected to the medical imaging apparatus, and may further include a computer device connected to an Internet cloud, the computer device being connected via the Internet to the medical imaging apparatus or a memory for storing medical images. The imaging method may be independently or jointly implemented by the aforementioned medical imaging apparatus, the computer device connected to the medical imaging apparatus, and the computer device connected to the Internet cloud.

For example, CT uses X-rays to carry out continuous profile scans around a part of a scanned subject, and a detector receives the X-rays that pass through said plane and converts the X-rays into visible light or converts a received photon signal directly and then reconstructs an image via a series of processes. MRI is based on the principle of the nuclear magnetic resonance of atomic nuclei, and forms an image via reconstruction by transmitting radio frequency pulses to the scanned subject and receiving electromagnetic signals emitted from the scanned subject.

PET uses a cyclotron to accelerate charged particles to bombard a target nucleus, which produces positron-bearing radionuclides by means of nuclear reactions and synthesizes imaging agents that are introduced into the body and localized in a target organ. The radionuclides emit positively charged electrons during a decay process, and after the positron travels a short distance in the tissue, the positron interacts with the electrons in the surrounding material and annihilation radiation occurs, from which two photons of equal energy are emitted in opposite directions. PET imaging uses a series of paired detectors that are arranged 180 degrees from each other and that receive coincidence lines to detect the photons of annihilating radiation produced by a tracer outside the body, and the collected information is processed by a computer to obtain a reconstructed image.

SPECT uses a radioactive isotope as a tracer, and the tracer is injected into the human body so that the tracer is concentrated on an organ to be examined, thus making the organ a source of γ-rays, and the distribution of radioactivity in organ tissue is recorded outside the body using detectors that rotate around the human body. One set of data is obtained when the detectors rotate to one angle and several sets of data can be obtained when the detectors rotate a full circle. From said data, a series of tomographic planar images can be created, and a computer reconstructs the imaging in a cross-sectional manner.

PET and SPECT extend a histopathological examination of local tissue from a molecular level to a biochemistry display, and the provided images are images of human physiological metabolism, which are distinguished for functional imaging and can detect functional and metabolic changes during the processes of disease occurrence and development, while CT and MRI are distinguished for the ability to accurately reflect morphological and structural changes. Among methods in the prior art, CT or MRI may be used for attenuation correction of PET or SPECT images. That is, PET or SPECT and CT or MRI are fused into one so that the functional and anatomical image information can be complementary to each other to achieve better identification and diagnosis.

In addition, a medical imaging workstation may be disposed locally relative to the medical imaging apparatus. That is, the medical imaging workstation is disposed adjacent to the medical imaging apparatus, and the medical imaging workstation and medical imaging apparatus may be located together in a scanning room, an imaging department, or in the same hospital. A medical image cloud platform analysis system may be located away from the medical imaging apparatus, e.g., arranged at a cloud end that is in communication with the medical imaging apparatus.

As an example, after a medical institution completes an imaging scan by using the medical imaging apparatus, data obtained by scanning is stored in a storage device. The medical imaging workstation may directly read the data obtained by scanning and perform image processing by means of a processor thereof. As another example, the medical image cloud platform analysis system may read a medical image in the storage device by means of remote communication to provide "software as a service (SAAS)." SAAS can exist between hospitals, between a hospital and an imaging center, or between a hospital and a third-party online diagnosis and treatment service provider. In the embodiments of the present application, the term "subject to be examined" may include any subject being imaged.

There are mainly three kinds of existing clinically-used CT scan modes: scout scan, axial scan, and spiral scan, where during the scout scan process, an X-ray tube and a detector are stationary, and a scanning bed is moved, thereby obtaining a large-range scout image; during the axial scan process, the scanning bed needs to be stepped to a position for imaging, then the movement of the scanning bed is stopped, and the tube and the detector are rotated 360° (or more than 360°) to acquire data, and then the tube and the detector stop working, whereby scanning work of a current layer is completed. Then, the scanning bed is once again stepped to a next position, the aforementioned scanning process is repeated, and scanning work of a next layer is completed, and so on; and during the spiral scan process, the scanning bed is also moved at a uniform speed during the rotation of the tube and the detector, thereby acquiring continuous data.

After a scout image is obtained by the scout scan, the scout image may provide a visualized body size and organ distribution of a subject to be examined, thereby assisting an operator in locating a scan region for the axial scan or spiral scan. The inventor found that during existing CT scan processes, after the scout scan, it is difficult for the operator to intuitively select or adjust appropriate scanning parameters in a scanning protocol to perform a formal diagnostic scan (e.g., an axial scan or a spiral scan), and therefore, the image quality obtained by the formal diagnostic scan cannot be guaranteed.

In view of at least one of the above technical problems, a computer device, and a medical image processing method, apparatus, and system are provided in the embodiments of the present application. A predicted section image corresponding to a first region of interest in a first scout image obtained by a scout scan is determined according to a preset correspondence between a scout image and a section image, and the predicted section image and scanning parameters corresponding to the predicted section image are displayed. Therefore, the operator can intuitively view the predicted section image and the scanning parameters corresponding to the predicted section image without a formal diagnostic scan, which helps the operator to confirm a scan range, select suitable scanning parameters, and evaluate the image quality.

The following is a specific description of an embodiment of the present invention with reference to the accompanying drawings. Provided in the embodiments of the present application is a medical image processing method, and FIG. 1 is a schematic diagram of the medical image processing method of the embodiments of the present application. As shown in FIG. 1, the medical image processing method includes acquiring a first scout image obtained after a scout scan is performed on a subject to be examined (block 101), determining, according to a preset correspondence between a scout image and a section image, a predicted section image corresponding to a first region of interest in the first scout image (block 102), and displaying the predicted section image and scanning parameters corresponding to the predicted section image (block 103).

Figure 2:
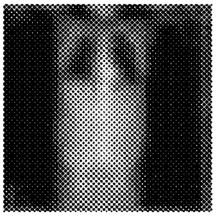
FIGS. 2 and 3 are schematic diagrams of a first scout image of the embodiments of the present application.
Figure 3:
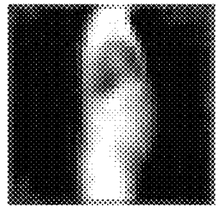

In some embodiments, a scout scan is performed on the subject to be examined, and the scout scan may be a whole body area scan or a local area scan defining a starting position and an ending position, e.g., the position of a workbench of an imaging system can be moved such that the scout scan is advanced from the starting position to the ending position, scan data is obtained by means of the scout scan, and image reconstruction is performed to obtain a first scout image which includes a normal scout image or a lateral scout image. FIGS. 2 and 3 are schematic diagrams of a normal scout image and a lateral scout image of the embodiments of the present application, respectively.

In some embodiments, in the prior art, a scout scan may be performed first to determine a scout image, a region of interest of a formal scan which includes a spiral scan or an axial scan or other scan modes is determined on the basis of the position of tissue to be imaged in the scout image, and after the formal scan is performed on the tissue to be imaged, a section image can be obtained, the section image referring to a section image of a section (e.g., a reference section) of a corresponding slice position of the tissue to be imaged (an anatomical image of a particular section). Taking the human body as an example, the section image may be a sagittal or transverse section image or the like of the human body, and the section image may also be referred to as a tomographic image, which is merely an example illustration herein, and the embodiments of the present application are not limited thereto.

In the embodiments of the present application, the predicted section image corresponding to the first region of interest in the first scout image can be determined without the formal scan according to the preset correspondence between the scout image and the section image, which helps the operator to evaluate the image quality according to the predicted section image, and to select suitable scanning parameters for the formal scan.

In some embodiments, the method may further include: determining the correspondence in advance, which is described in detail below.

In some embodiments, the correspondence may be determined on the basis of a deep learning algorithm or a machine learning algorithm, whereby training data including training input data and training output data is first acquired, the training input data including a scout image obtained by performing a scout scan in advance on a subject under examination, and the training output data including a section image obtained by performing an axial scan or a spiral scan on a region of interest of the subject under examination or an index identifier of the section image; and the training data is used to train a neural network model so as to obtain the correspondence.

For example, a large number of real clinical scout images obtained by performing scout scans on different subjects under examination may be collected and taken as training input data, and subject-under-examination features and/or regions of interest which correspond to different training input data are different, the subject-under-examination features including at least one of: body size, sex and age. That is, the training input data has parameters of at least the following several dimensions: subject-under-examination body size, subject-under-examination sex, subject-under-examination age, and region of interest (which is manually delimited or corresponds to a scanning protocol). For example, for a subject under examination corresponding to training input data 1, the body size is "height 180 cm, weight 80 kg", the sex is "male", the age is "30", and the region of interest is "chest"; for a subject under examination corresponding to training input data 2, the body size is "height 180 cm, weight 80 kg", the sex is "male", the age is "30", and the region of interest is "head"; for a subject under examination corresponding to training input data 3, the body size is "height 150 cm, weight 50 kg", the sex is "male", the age is "12", and the region of interest is "head"; for a subject under examination corresponding to training input data 4, the body size is "height 140 cm, weight 40 kg", the sex is "female", the age is "12", and the region of interest is "abdomen"; for a subject under examination corresponding to training input data 5, the body size is "height 150 cm, weight 60 kg", the sex is "female", the age is "70", and the region of interest is "abdomen", and so on, and the remainder will not be listed herein one by one. In order to improve the training effect, the training input data can cover scout images of various ages, various regions of interest, and various body sizes and ages.

For example, a large number of real clinical section images obtained by performing formal scans on different subjects under examination may be collected, and optionally, a unique index identifier may be set for each section image. The section images or the index identifiers of the section images are used as the training output data. Subject-under-examination features and/or regions of interest which correspond to different training output data are different, that is, the training output data has parameters of at least the following several dimensions: subject-under-examination body size, subject-under-examination sex, subject-under-examination age, and region of interest (which is manually delimited or corresponds to a scanning protocol). For example, for a subject under examination corresponding to training output data 1, the body size is "height 180 cm, weight 80 kg", the sex is "male", the age is "30", and the region of interest is "chest"; for a subject under examination corresponding to training output data 2, the body size is "height 180 cm, weight 80 kg", the sex is "male", the age is "30", and the region of interest is "head"; for a subject under examination corresponding to training output data 3, the body size is "height 150 cm, weight 50 kg", the sex is "male", the age is "12", and the region of interest is "head"; for a subject under examination corresponding to training output data 4, the body size is "height 140 cm, weight 40 kg", the sex is "female", the age is "12", and the region of interest is "abdomen"; for a subject under examination corresponding to training output data 5, the body size is "height 150 cm, weight 60 kg", the sex is "female", the age is "70", and the region of interest is "abdomen", and so on, and the remainder will not be listed herein one by one. It should be noted that the section image and the scout image correspond to each other, that is, the parameters of the aforementioned several dimensions of a pair of training input data and training output data used for training the neural network model are exactly the same, and are obtained by performing a scout scan and a formal scan on the same region of interest of the same subject under examination respectively.

In some embodiments, in order to make a training set more complete, the collected real clinical section images may be processed to obtain simulated section images, and optionally, a unique index identifier may be set for each simulated section image. The simulated section images or the index identifiers of the simulated section images, and the real section images or the index identifiers of the real section images are all used as the training output data, e.g., to simulate different scanning parameters, the scanning parameters including at least one of a noise index, a scan tube current and a scanning voltage. The real section images are processed by using a simulation algorithm, whereby simulated section images which have different scanning parameters are obtained, that is, there are at least two pieces of training output data which have different scanning parameters. Different scanning parameters means that at least one of the noise index, the scan tube current and the scanning voltage is different. The specific simulation algorithm may refer to related technologies which will not be repeated herein.

For example, the training output data has parameters of at least the following several dimensions: subject-under-examination body size, subject-under-examination sex, subject-under-examination age, region of interest (which is manually delimited or corresponds to a scanning protocol) and noise index (a scan tube current, a scanning voltage, etc. are also included, and only the scanning parameter acting as the noise index is taken as an example for illustration purposes). For a subject under examination corresponding to training output data 1 (real), the body size is "height 180 cm, weight 80 kg", the sex is "male", the age is "30", the region of interest is "chest", and the noise index is 10, and for a subject under examination corresponding to training output data 1A (simulated), the body size is "height 180 cm, weight 80 kg", the sex is "male", the age is "30", the region of interest is "chest", and the noise index is 5; for a subject under examination corresponding to training output data 2 (real), the body size is "height 180 cm, weight 80 kg", the sex is "male", the age is "30", the region of interest is "head", and the noise index is 10, and for a subject under examination corresponding to training output data 2A (simulated), the body size is "height 180 cm, weight 80 kg", the sex is "male", the age is "30", the region of interest is "head", and the noise index is 5; for a subject under examination corresponding to training output data 3 (real), the body size is "height 150 cm, weight 50 kg", the sex is "male", the age is "12", the region of interest is "head", and the noise index is 10, and for a subject under examination corresponding to training output data 3A (simulated), the body size is "height 150 cm, weight 50 kg", the sex is "male", the age is "12", the region of interest is "head", and the noise index is 5; for a subject under examination corresponding to training output data 4 (real), the body size is "height 140 cm, weight 40 kg", the sex is "female", the age is "12", the region of interest is "abdomen", and the noise index is 10, and for a subject under examination corresponding to training output data 4A (simulated), the body size is "height 140 cm, weight 40 kg", the sex is "female", the age is "12", the region of interest is "abdomen", and the noise index is 5; for a subject under examination corresponding to training output data 5 (real), the body size is "height 150 cm, weight 60 kg", the sex is "female", the age is "70", the region of interest is "abdomen", and the noise index is 10, and for a subject under examination corresponding to training output data 5A (simulated), the body size is "height 150 cm, weight 60 kg", the sex is "female", the age is "70", the region of interest is "abdomen", and the noise index is 5, and so on, and the remainder will not be listed herein one by one.

It should be noted that the real section image, the simulated section image and the scout image correspond to each other, that is, the pair of training input data and training output data used for training the neural network model are obtained by performing a scout scan and a formal scan respectively for the same region of interest of the same subject under examination, or are obtained by performing a scout scan and performing simulation after the formal scan respectively for the same region of interest of the same subject under examination.

In some embodiments, the correspondence is obtained by using the aforementioned training data to train the neural network model, i.e. training by means of using the training input data as an input to the neural network model, and using the training output data as an output received from the neural network model. The above neural network model is composed of an input layer, an output layer, and one or more hidden layers (a convolutional layer, a pooling layer, a normalization layer, etc.) between the input layer and the output layer. Each layer can consist of multiple processing nodes that can be referred to as neurons. For example, the input layer may have neurons for each pixel or set of pixels from the scan plane of an anatomical structure. The output layer may have neurons corresponding to a plurality of predefined structures or predefined types of structures (or organizations therein). Each neuron in each layer may perform processing functions and pass processed medical image information to one of a plurality of neurons in a downstream layer for further processing. That is, in correspondence with "simple" features extracted from input data, an earlier or higher-level layer can then become, by means of combining the simple features, a layer exhibiting features of higher complexity. In practice, each layer (or more specifically, each "neuron" in each layer) may process input data as output data for representation by using one or a plurality of linear and/or non-linear transformations (so-called activation functions). The number of the plurality of "neurons" may be constant among the plurality of layers or may vary from layer to layer. For example, neurons in the first layer may learn to recognize structural edges in medical image data. Neurons in the second layer may learn to recognize shapes etc., on the basis of the detected edges from the first layer. The structure of a first neural network model and a second neural network model may be, for example, the structure of a VGG16 model, a GoogleNet model, or a ResUNet model, etc. The embodiments of the present application are not limited thereto, and the structure of the above models may refer to related technologies, which will not be detailed herein. The training process is based on the training data, the number of neurons in the neural network is set and network parameters (including but not limited to weights, biases, etc.) are optimized to identify a mathematical relationship between a known input and a desired output and to characterize a mathematical relationship between an input and an output of each layer, such that a loss function converges, so as to obtain the aforementioned neural network by training. The loss function may be a cross-entropy function, but the embodiments of the present application are not limited thereto.

In some embodiments, in block 102, an image of the first region of interest of the first scout image may be input into the trained neural network model, and the neural network model may output a section image corresponding to the first region of interest of the first scout image and an index identifier of the section image so as to determine the predicted section image.

Figure 5:
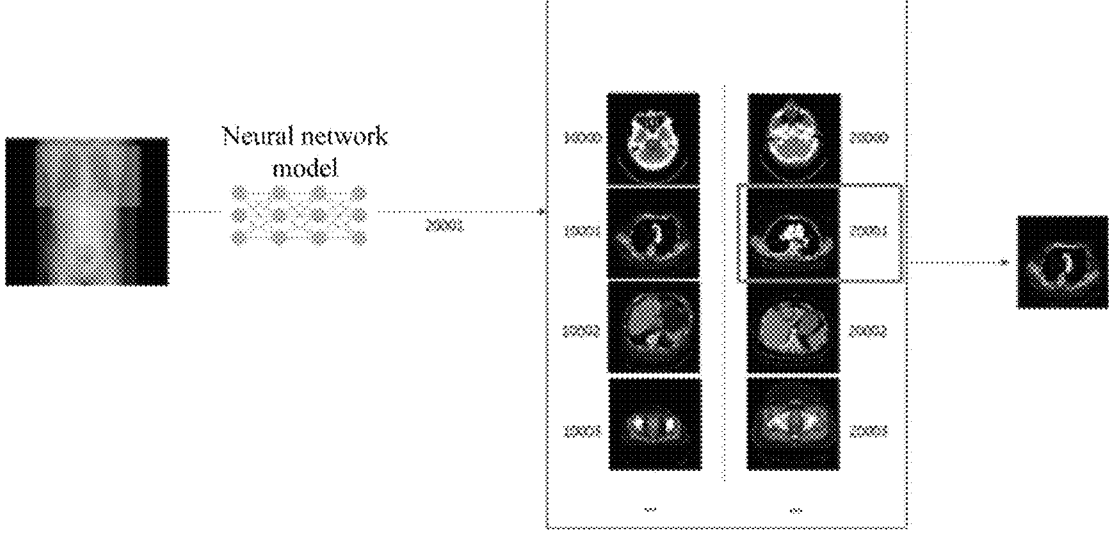
FIG. 5 is a schematic diagram for determining a predicted section image of the embodiments of the present application.

FIG. 5 is a schematic diagram for determining a predicted section image of the embodiments of the present application. As shown in FIG. 5, the first region of interest of the first scout image is a rectangular region in the diagram. The first region of interest is inputted into the neural network model, an index identifier 20001 of the predicted section image is outputted, and a corresponding predicted section image is obtained via searching in the training output data according to the index identifier.

In some embodiments, in addition to determining the correspondence by using a deep learning or machine learning algorithm, the aforementioned obtained training input data and training output data may be directly associatively stored in a database to obtain the correspondence. The embodiments of the present application are not limited thereto.

Figure 4:
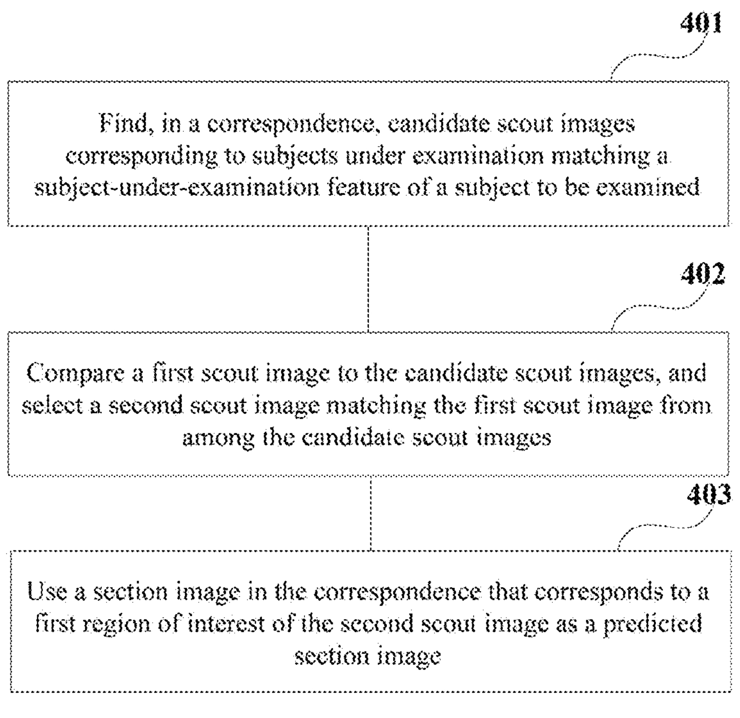
FIG. 4 is a schematic diagram of an implementation of operation 102 of the embodiments of the present application.

FIG. 4 is a schematic diagram of an implementation of block 102 of the embodiments of the present application. As shown in FIG. 4, operations of block 102 include finding, in the correspondence, candidate scout images corresponding to subjects under examination matching a subject-under-examination feature of the subject to be examined (block 401), comparing the first scout image to the candidate scout images, and selecting a second scout image matching the first scout image from among the candidate scout images (block 402), and using a section image in the correspondence that corresponds to a first region of interest of the second scout image as the predicted section image (block 403).

In some embodiments, in 401, the subjects under examination matching the subject-under-examination feature of the subject to be examined may be found in a database including the correspondence by means of string matching and other methods, where matching means that the subject-under-examination features are consistent. For example, a subject under examination consistent with the body size, sex and age of the subject to be examined may be found in the database, training input data of one or more subjects under examination matching the feature is used as the candidate scout image, and the candidate scout image may be one or more candidate scout images.

In some embodiments, in 402, the first scout image is compared to the one or more candidate scout images by using an image matching algorithm. The image matching algorithm may employ the related technologies, and the embodiments of the present application are not limited thereto. When the candidate scout image is a plurality of candidate scout images, a second scout image matching the first scout image is selected from among the candidate scout images. But 402 is optional, for example, when the candidate scout image is one candidate scout image, the candidate scout image may be used directly as the second scout image.

In some embodiments, in 403, a section image (or rather training output data) corresponding to the first region of interest of the second scout image may be found in the database including the correspondence, and is taken as the predicted section image.

In some embodiments, in the existing methods, during medical imaging system scanning protocol management and actual scanning processes, only scanning parameters, that is, parameter names and corresponding parameter values, are displayed on a display interface of a display, and an intuitive illustration is not displayed on the display interface. In the embodiments of the present application, a new display interface may be designed on which the predicted section image and the scanning parameters corresponding to the predicted section image are displayed. Therefore, the operator can intuitively view, without a formal diagnostic scan, the image quality of the predicted section image which can be obtained by scanning and simulating using the currently displayed scanning parameters, which helps the operator to determine whether the current scanning parameters are suitable or need to be adjusted, i.e., to select suitable scanning parameters for the formal scan.

Figure 6:
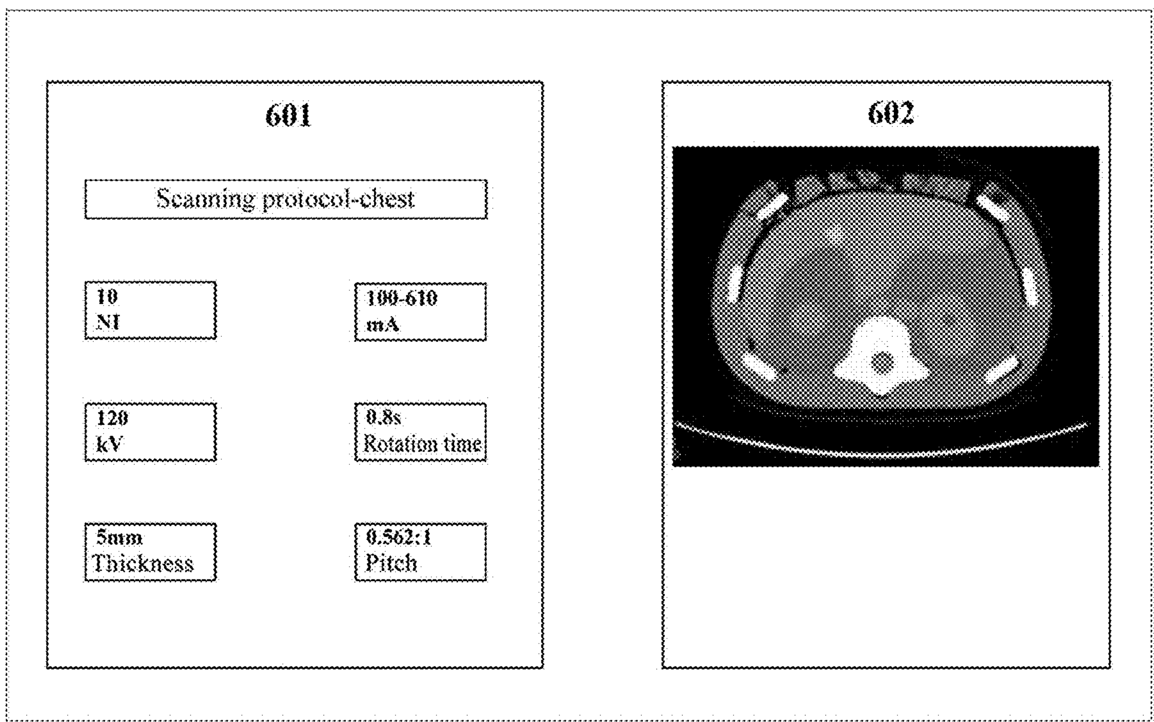
FIG. 6 is a schematic diagram of a display interface of the embodiments of the present application.

FIG. 6 is a schematic diagram of a display interface of the embodiments of the present application. As shown in FIG. 6, the display interface includes a parameter display region 601 and a section image preview region 602, where the section image preview area 602 displays a predicted section image, and the parameter display region 601 displays scanning parameters, such as a noise index NI, a scan tube current mA and a scanning voltage kV, corresponding to the predicted section image currently displayed in the section image preview region 602. Optionally, the scanning parameters may further include: slice thickness, pitch, rotation time, and the like. Optionally, the display interface may also show a first scout image and a first region of interest, and the embodiments of the present application are not limited thereto.

In some embodiments, the predicted section image may be updated according to an adjusted first region of interest, and the updated predicted section image and scanning parameters corresponding to the updated predicted section image may be displayed in real time. The operator may adjust the first region of interest (change a scan range), and the aforementioned operation 102 is repeated, i.e., a predicted section image corresponding to the updated first region of interest (hereinafter referred to as a second region of interest) is determined according to the correspondence, e.g., an image of the updated first region of interest of the first scout image is inputted into the trained neural network model to obtain the updated predicted section image, and the updated predicted section image and scanning parameters corresponding to the updated predicted section image are displayed in the section image preview region 602 in real time.

In some embodiments, the predicted section image may be updated according to adjusted scanning parameters, and the updated predicted section image and scanning parameters corresponding to the updated predicted section image may be displayed in real time. The operator may manually adjust the scanning parameters in the parameter display region 601 in FIG. 6, e.g., by typing new scanning parameters by means of an input device, and the predicted section image is processed according to the adjusted scanning parameters to obtain the updated predicted section image. For example, a current scanning parameter noise index is 5, the operator adjusts the noise index to 10, and a current predicted section image is processed into a predicted section image having a noise index of 10, and the updated predicted section image is displayed in the section image preview region 602 in real time. As such, the predicted section image may vary along with adjustments to the scanning parameters, and the changed predicted section image is displayed in real time. Thus, the operator can intuitively view the image quality of the predicted section image which can be obtained by scanning and simulating by using the displayed scanning parameters, which helps the operator to determine whether the adjusted scanning parameters are suitable, so as to select suitable scanning parameters for the formal scan.

In some embodiments, the method may further include: determining scanning parameters for clinical use according to the updated predicted section image and the scanning parameters corresponding to the updated predicted section image, and using the scanning parameters for clinical use to perform an axial scan or a spiral scan on a subject to be examined so as to obtain a diagnostic section image. For example, by comparing the image quality of the updated predicted section image and the predicted section image before updating, scanning parameters of a predicted section image of a better image quality may be selected as the scanning parameters for clinical use. For example, the current scanning parameter noise index is 5, and a predicted section image A1 is displayed in the section image preview region 602 in real time; the operator adjusts the noise index to 10, and an updated predicted section image A2 is displayed in the section image preview region 602 in real time; and the operator adjusts the noise index to 15, and an updated predicted section image A2 is displayed in the section image preview region 602 in real time. The image quality of the predicted section images A1, A2, and A3 are compared, and after comparison, it is assumed that the image quality of the predicted section image A2 when the noise index is 10 is better, then the noise index 10 is used as the noise index for the clinical scan, and an axial scan or spiral scan is performed on the subject to be examined by using the noise index 10 so as to obtain a diagnostic section image.

Figure 7:
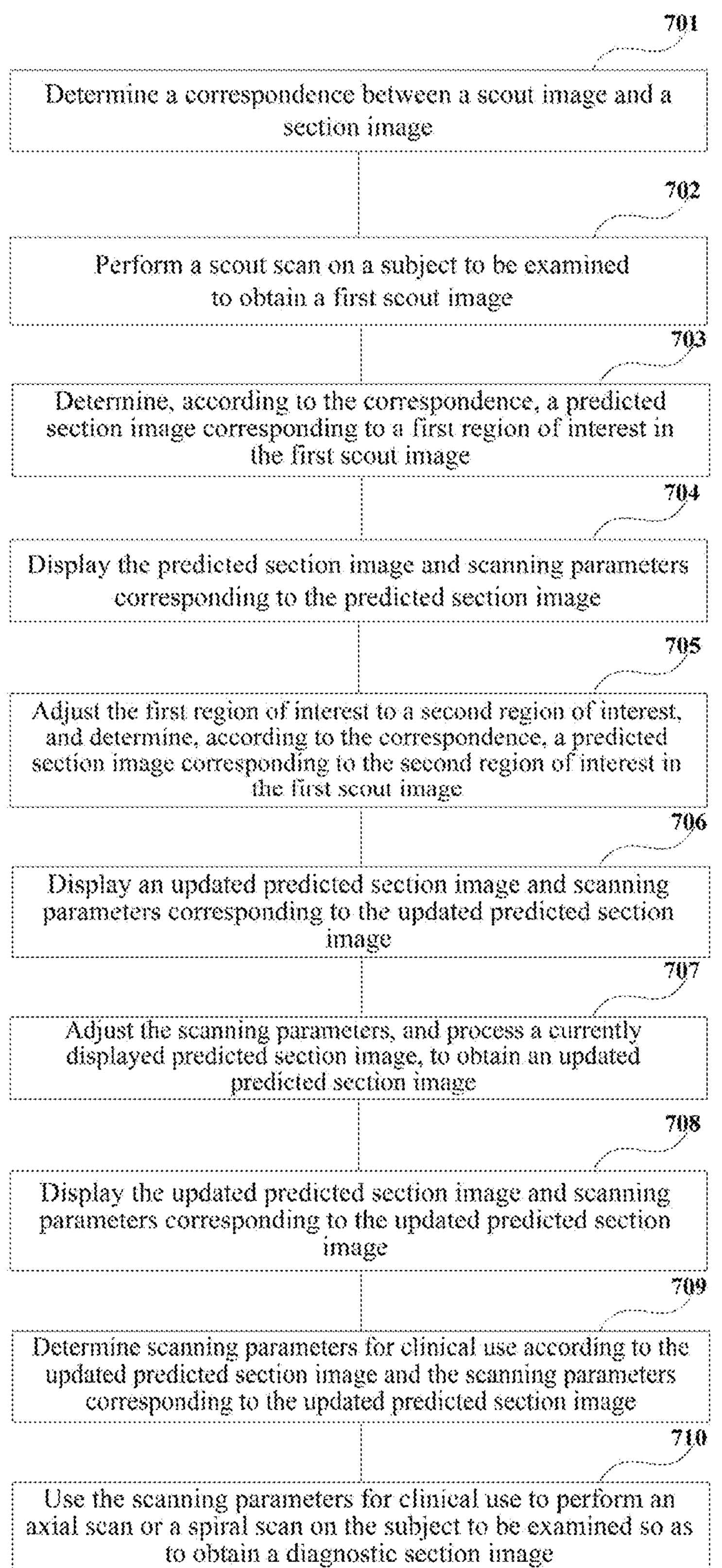
FIG. 7 is a schematic diagram of the medical image processing method of the embodiments of the present application.

FIG. 7 is a schematic diagram of the medical image processing method of the embodiments of the present application. As shown in FIG. 7, the method includes determining a correspondence between a scout image and a section image (block 701), performing a scout scan on a subject to be examined to obtain a first scout image (block 702), determining, according to the correspondence, a predicted section image corresponding to a first region of interest in the first scout image (block 703), displaying the predicted section image and scanning parameters corresponding to the predicted section image (block 704), adjusting the first region of interest to a second region of interest, and determining, according to the correspondence, a predicted section image corresponding to the second region of interest in the first scout image (block 705), displaying an updated predicted section image and scanning parameters corresponding to the updated predicted section image (block 706), adjusting the scanning parameters, and processing a currently displayed predicted section image, to obtain an updated predicted section image (block 707), displaying the updated predicted section image and scanning parameters corresponding to the updated predicted section image (block 708), determining scanning parameters for clinical use according to the updated predicted section image and the scanning parameters corresponding to the updated predicted section image (block 709), and using the scanning parameters for clinical use to perform an axial scan or a spiral scan on the subject to be examined so as to obtain a diagnostic section image (block 710).

It should be noted that FIG. 7 merely schematically illustrates the embodiment of the present application above, but that the present application is not limited thereto. For example, the order of execution between operations may be suitably adjusted. In addition, some other operations may also be added or some of the operations may be omitted. Those skilled in the art can make appropriate modifications according to the aforementioned content, rather than being limited by the disclosure of FIG. 7.

As can be seen from the above embodiments, a predicted section image corresponding to a first region of interest in a first scout image obtained by a scout scan is determined according to a preset correspondence between a scout image and a section image, and the predicted section image and scanning parameters corresponding to the predicted section image are displayed. Therefore, the operator can intuitively view the predicted section image and the scanning parameters corresponding to the predicted section image without a formal diagnostic scan, which helps the operator to confirm a scan range, select suitable scanning parameters, and evaluate the image quality.

Figure 8:
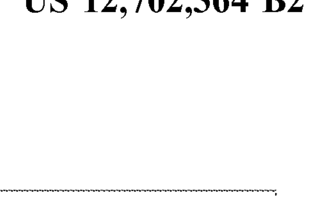
FIG. 8 is a schematic diagram of a medical image processing apparatus of the embodiments of the present application.
Figure 8:
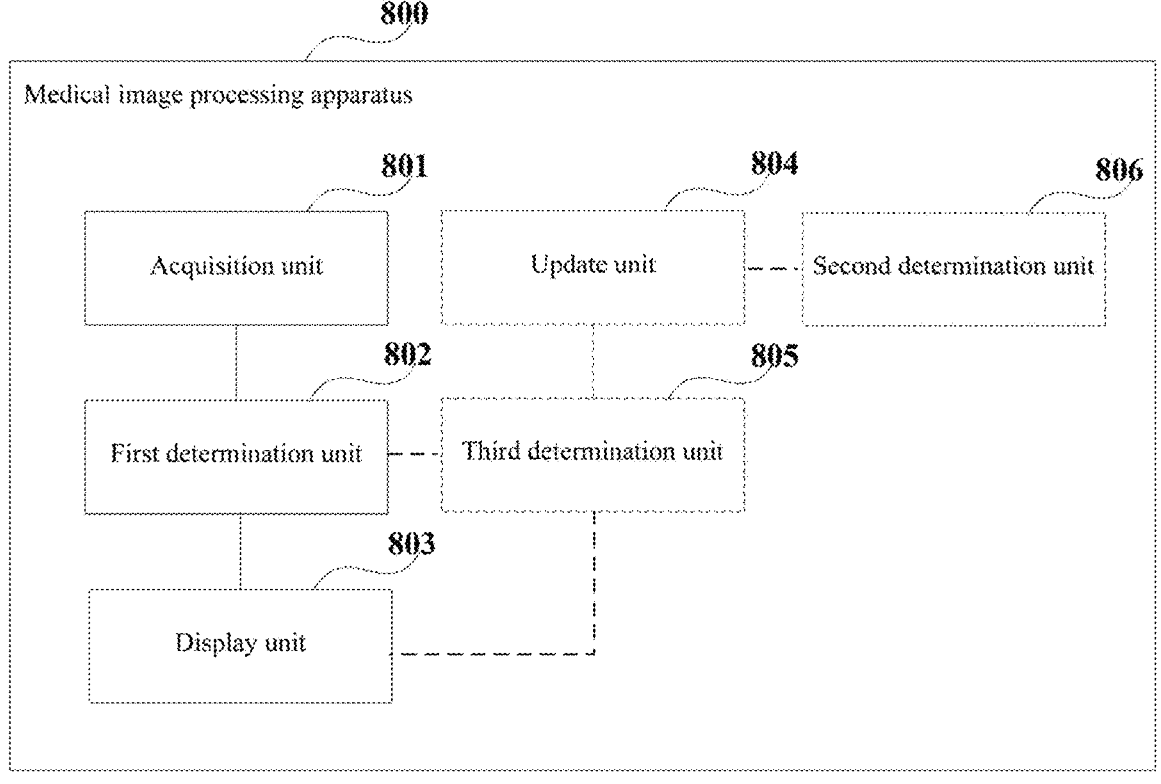

Further provided in the embodiments of the present application is a medical image processing apparatus, and repetitive content from the aforementioned embodiments are not repeated herein. FIG. 8 is a schematic diagram of the medical image processing apparatus of the embodiments of the present application. As shown in FIG. 8, the medical image process apparatus 800 includes an acquisition unit 801, which acquires a first scout image obtained after a scout scan is performed on a subject to be examined, a first determination unit 802, which determines, according to a preset correspondence between a scout image and a section image, a predicted section image corresponding to a first region of interest in the first scout image, and a display unit 803, which displays the predicted section image and scanning parameters corresponding to the predicted section image.

In some embodiments, the apparatus may further include an update unit 804, which updates the predicted section image according to adjusted scanning parameters and/or according to an adjusted first region of interest, wherein the display unit 803 displays in real time the updated predicted section image and scanning parameters corresponding to the updated predicted section image.

In some embodiments, the apparatus may further include a second determination unit 805, which determines scanning parameters for clinical use according to the updated predicted section image and the scanning parameters corresponding to the updated predicted section image, and uses the scanning parameters for clinical use to perform an axial scan or a spiral scan on the subject to be examined so as to obtain a diagnostic section image.

In some embodiments, the apparatus may further include a third determination unit 806, which determines the correspondence on the basis of a deep learning algorithm or a machine learning algorithm.

Figure 9:
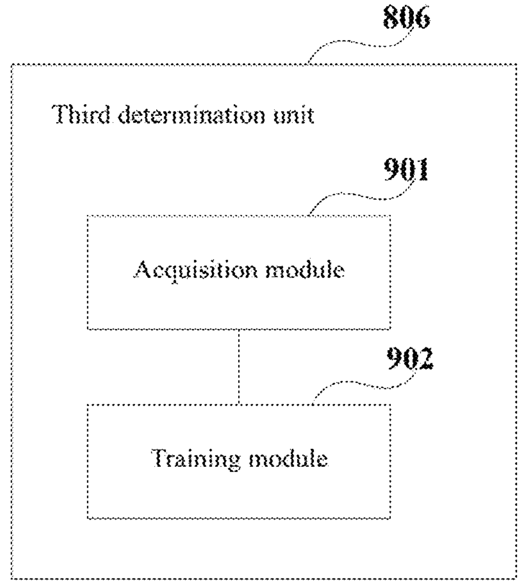
FIG. 9 is a schematic diagram of an implementation of a third determination unit of the embodiments of the present application.

FIG. 9 is a schematic diagram of the third determination unit 806 of the embodiments of the present application. As shown in FIG. 9, the third determination unit 806 includes an acquisition module 901, which acquires training data, the training data comprising training input data and training output data, the training input data comprising a scout image obtained by performing a scout scan in advance on a subject under examination, and the training output data comprising a section image obtained by performing an axial scan or a spiral scan on a region of interest of the subject under examination or an index identifier of the section image. The third determination unit 806 also includes a training module 902, which uses the training data to train a neural network model so as to obtain the correspondence.

Figure 10:
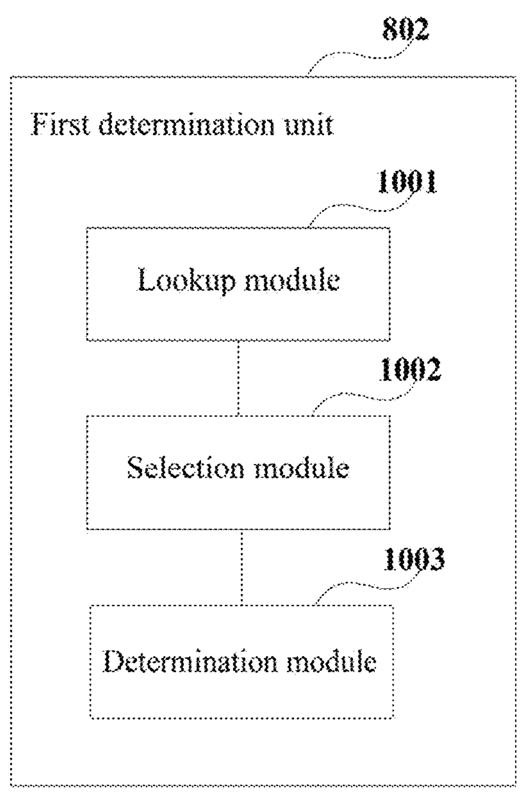
FIG. 10 is a schematic diagram of an implementation of a first determination unit of the embodiments of the present application.

In some embodiments, the first determination unit 802 inputs an image of the first region of interest of the first scout image into the trained neural network model to obtain the predicted section image. FIG. 10 is a schematic diagram of an implementation of the first determination unit 802 of the embodiments of the present application, which includes a lookup module 1001, which finds, in the correspondence, candidate scout images corresponding to subjects under examination matching a subject-under-examination feature of the subject to be examined, a selection module 1002, which compares the first scout image to the candidate scout images, and selects a second scout image matching the first scout image from among the candidate scout images, and a determination module 1003, which uses a section image in the correspondence that corresponds to a first region of interest of the second scout image as the predicted section image.

In some embodiments, the functions of unit modules other than the display unit may be integrated into a processor for implementation. The processor is configured to implement the medical image processing method as described in the aforementioned embodiments. The processor may also be referred to as a microcontroller unit (MCU), microprocessor or microcontroller or another processor device and/or logic device. The processor may include a reset circuit, a clock circuit, a chip, a microcontroller, and so on. The functions of the processor may be integrated on a main board of a medical device (e.g., the processor is configured as a chip connected to a main board processor (CPU)), or may be configured independently of the main board, and embodiments of the present invention are not limited thereto.

As can be seen from the above embodiments, a predicted section image corresponding to a first region of interest in a first scout image obtained by a scout scan is determined according to a preset correspondence between a scout image and a section image, and the predicted section image and scanning parameters corresponding to the predicted section image are displayed Therefore, the operator can intuitively view the predicted section image and the scanning parameters corresponding to the predicted section image without a formal diagnostic scan, which helps the operator to confirm a scan range, select suitable scanning parameters, and evaluate the image quality.

Figure 11:
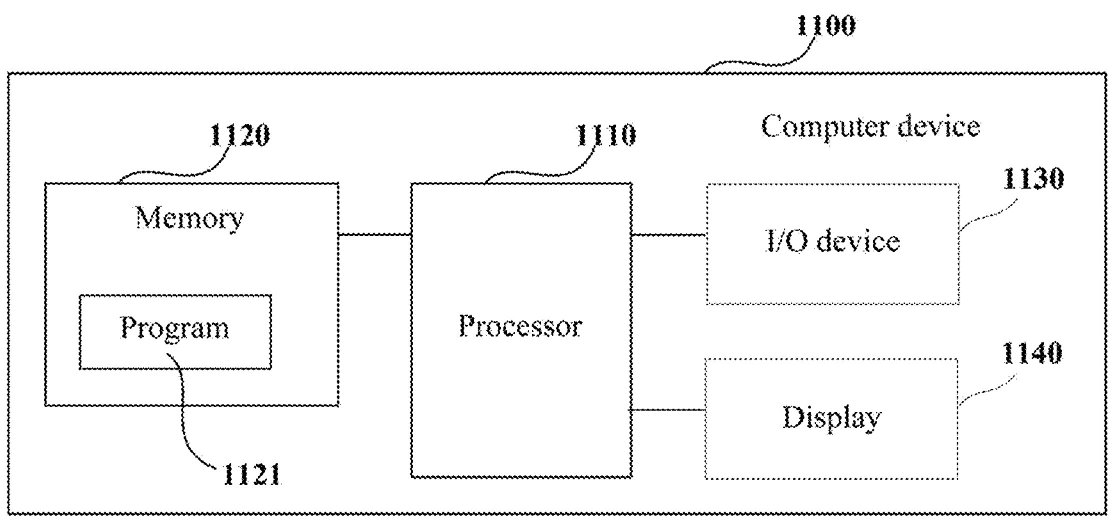
FIG. 11 is a schematic diagram of a computer device of the embodiments of the present application.

Further provided in the embodiments of the present application is a computer device, and FIG. 11 is a schematic diagram of the computer device of the embodiments of the present application. As shown in FIG. 11, the computer device 1100 may include: one or more processors (e.g., a central processing unit (CPU)) 1110, and one or more memories 1120, the memory 1120 being coupled to the processor 1110. The memory 1120 can store image frames, neural network models, etc., in addition, may further include a program 1121 for medical image processing, and executes the program 1121 under the control of the processor 1110. The memory 1120 may include, for example, a ROM, a floppy disk, a hard disk, an optical disk, a magneto-optical disk, a CD-ROM, or a non-volatile memory card.

In some embodiments, the functions of the medical image processing apparatus 800 are integrated into the processor 1110 for implementation. The processor 1110 is configured to implement the medical image processing method as described in the aforementioned embodiments. For the implementation of the processor 1110, reference may be made to the aforementioned embodiments, which will not be repeated herein.

In some embodiments, the medical image processing apparatus 800 and the processor 1110 are configured separately, e.g., the medical image processing apparatus 800 can be configured as a chip connected to the processor 1110, and the functions of the medical image processing apparatus 800 can be achieved by means of the control of the processor 1110.

In addition, as shown in FIG. 11, the computer device 1100 may further include: an input device 1130 and a display 1140 (which displays a user graphics interface, and various data, image frames, or parameters generated during data acquisition and processing processes), etc., wherein the functions of the above components are similar to the prior art, and will not be repeated herein. It should be noted that the computer device 1100 does not necessarily include all of the components shown in FIG. 11. In addition, the computer device 1100 may further include components not shown in FIG. 11, for which reference may be made to the related technologies.

The processor 1110 may communicate with a medical device, the display, etc. in response to an operation of the input device, and may also control input actions and/or states of the input device. The processor 1110 may also be referred to as a microcontroller unit (MCU), microprocessor or microcontroller or another processor device and/or logic device. The processor 1110 may include a reset circuit, a clock circuit, a chip, a microcontroller, and so on. The functions of the processor 1110 may be integrated on a main board of the medical device (e.g., the processor 1110 is configured as a chip connected to the main board processor (CPU)), or may be configured independently of the main board, and the embodiments of the present invention are not limited thereto.

In some embodiments, the computer device may be a computer server or a cloud platform or workstation, etc., and the embodiments of the present invention are not limited thereto.

Figure 12:
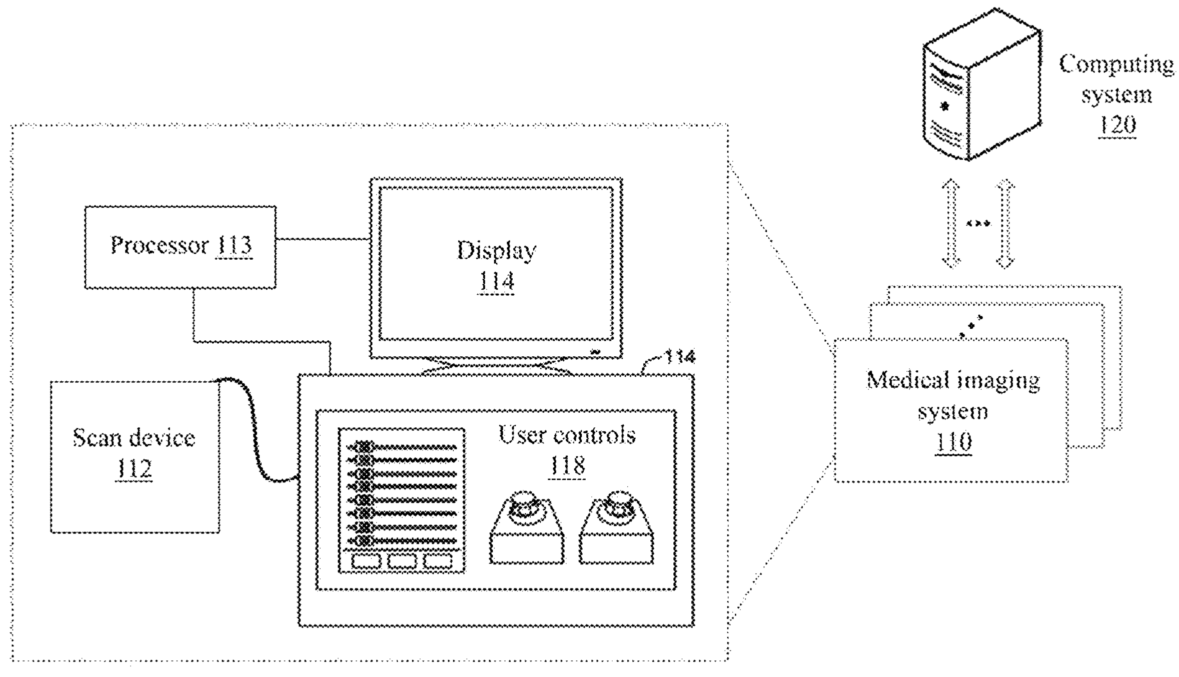
FIG. 12 is a schematic diagram of a medical image processing system of the embodiments of the present application.

Further provided in the embodiments of the present application is a medical image processing system, and FIG. 12 is a schematic diagram of a medical image processing system of the embodiments of the present application. As shown in FIG. 12, the medical image processing system 110 includes suitable hardware, software, or a combination thereof for supporting medical image processing (i.e., enabling the acquisition of data for use in generating and/or rendering images during a medical image processing examination). For example, the medical image processing system 110 may be an ultrasound system or magnetic resonance system, etc. configured to generate and/or render ultrasound images. As shown in FIG. 12, the medical image processing system 110 may include a scan device 112, a display 114, and a processor 113, and the scan device may be movable.

The scan device 112 may be configured to generate and/or capture specific types of imaging signals (and/or data corresponding thereto) by means such as moving over a subject to be examined (or a portion thereof), and may include suitable circuits for performing and/or supporting such functions. The scan device 112 may be an ultrasonic probe, an MRI scanner, a CT scanner, or any suitable imaging device.

The display 114 may be configured to display images (e.g., via a screen). In some cases, the display 114 may also be configured to at least partially generate the displayed image. In addition, the display 114 may further support user input/output. For example, in addition to images, the display 114 may further provide (e.g., via the screen) user feedback (e.g., information related to a system, functions thereof, settings thereof, etc.). The display 114 may further support user input (e.g., via user controls 118) to, for example, allow for the control of medical image processing. User input can involve controlling the display of images, selecting settings, specifying user preferences, requesting feedback, etc.

In some embodiments, the medical image processing system 110 may further incorporate additional and dedicated computing resources, such as one or more computing systems 120. In this regard, each computing system 120 may include circuits suitable, interfaces, logic, and/or code for processing, storing, and/or communicating data. The computing system 120 may be a dedicated device configured for use specifically in conjunction with medical image processing, or may be a general-purpose computing system (e.g., a personal computer, server, etc.) that is set up and/or configured to perform the operations described below with respect to computing system 120. The computing system 120 may be configured to support the operation of the medical image processing system 110, as described below. In this regard, various functions and/or operations can be offloaded from an imaging system, which may simplify and/or centralize certain aspects of processing to reduce costs (by eliminating the need to add processing resources to the imaging system).

The computing system 120 may be set up and/or arranged for use in different ways. For example, in some implementations, a single computing system 120 may be used, and in other implementations, multiple computing systems 120 are configured to work together (e.g., on the basis of a distributed processing configuration), or work individually, wherein each computing system 120 is configured to process specific aspects and/or functions, and/or to process data only for a specific medical image processing system 110.

In some embodiments, the computing system 120 may be local (e.g., co-located with one or more medical image processing systems 110, such as within the same facility and/or the same local network); and in other implementations, the computing system 120 may be remote, and thus accessible only via a remote connection (e.g., via the Internet or other available remote access technology). In particular specific implementations, the computing system 120 may be configured in a cloud-based manner and may be accessed and/or used in a substantially similar manner to accessing and using other cloud-based systems.

Once the data is generated and/or configured in the computing system 120, the data can be copied and/or loaded into the medical image processing system 110 in different ways. For example, data may be loaded by means of a directional connection or link between the medical image processing system 110 and the computing system 120. In this regard, communication between the different components of the setup can be performed using available wired and/or wireless connections and/or according to any suitable communication (and/or networking) standards or protocols. Optionally or additionally, the data may be loaded indirectly into the medical image processing system 110. For example, data may be stored in a suitable machine-readable medium (e.g., flash memory card, etc.) and then loaded into the medical image processing system 110 by using the machine-readable medium (onsite, such as by a user of the system (e.g., imaging clinician) or authorized personnel); or the data may be downloaded to a locally communicative electronic device (e.g., laptop, etc.) and then said electronic device is used onsite (e.g., by a user of the system or authorized personnel) to upload the data to the medical image processing system 110 via a direct connection (e.g., USB connector, etc.).

During an operation, the medical image processing system 110 may be used to generate and present (e.g., render or display) images during a medical examination, and/or is used in conjunction therewith to support user input/output. The images can be 2D, 3D, and/or 4D images. The particular operations or functions performed in the medical image processing system 110 which facilitate the generation and/or presentation of images depend on the type of system (i.e., the means used to obtain and/or generate the data corresponding to the images).

In some embodiments, the scan device 112 performs a scout scan on the subject to be examined to obtain imaging data, the processor 113 generates a first scout image according to the imaging data, and determines a predicted section image according to a correspondence, and the display 114 may display the predicted section image and corresponding scanning parameters in real time. The specific implementations are described as above, and will not be repeated herein.

Figure 13:
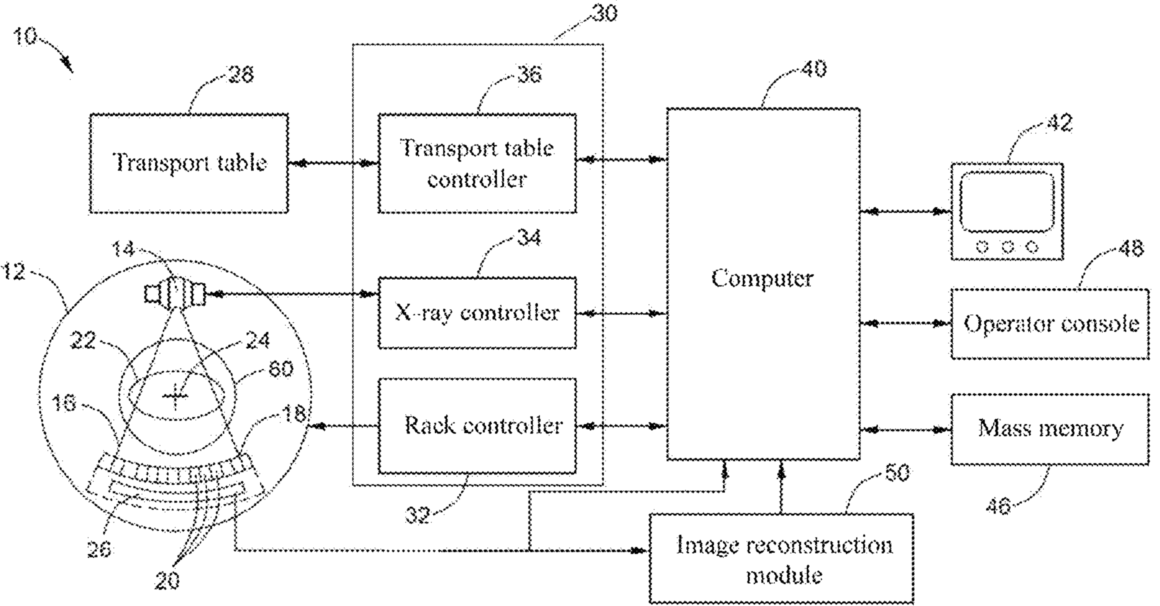
FIG. 13 is a schematic diagram of a CT system of the embodiments of the present application.

An example description in which the medical imaging system is taken as a CT system is given below, and FIG. 13 is a schematic diagram of a CT system 10 of the embodiments of the present application. As shown in FIG. 13, the system 10 includes a rack 12. An X-ray source 14 and a detector 18 are arranged opposite to each other on the rack 12. The detector 18 is composed of a plurality of detector modules 20 and a data acquisition system (DAS) 26. The DAS 26 is configured to convert sampled analog data of analog attenuation data received by the plurality of detector modules 20 into digital signals for subsequent processing.

In some embodiments, the system 10 is used for acquiring, from different angles, projection data of a subject to be examined. Thus, components on the rack 12 are used for rotating around a rotation center 24 to acquire projection data. During rotation, the X-ray radiation source 14 is configured to emit X-rays 16 that penetrate the subject to be examined toward the detector 18. Attenuated X-ray beam data is preprocessed and then used as projection data of a target volume of the subject. An image of the subject to be examined may be reconstructed on the basis of the projection data. The reconstructed image may display internal features of the subject to be examined. Said features include, for example, the lesions, size, and shape of a body tissue structure. The rotation center 24 of the rack also defines the center of a scanning field 80.

In some embodiments, the system 10 includes a control mechanism 30. The control mechanism 30 may include an X-ray controller 34 which is configured to provide power and timing signals to the X-ray radiation source 14. The control mechanism 30 may further include a rack controller 32 which is configured to control the rotational speed and/or position of the rack 12 on the basis of imaging requirements. The control mechanism 30 may further include a transport table controller 36 which is configured to drive a transport table 28 to move to a suitable position so as to position the subject to be examined in the rack 12 to perform a scout scan or an axial scan or a bolt scan or other scan modes in order to acquire the projection data of the target volume of the subject to be examined. Furthermore, the transport table 28 includes a driving device, and the transport table controller 36 may control the transport table 28 by means of controlling the driving device.

The system 10 further includes an image reconstruction module 50. As described above, the DAS 26 samples and digitizes the projection data acquired by the plurality of detector modules 20. Next, the image reconstruction module 50 performs high-speed image reconstruction on the basis of the aforementioned sampled and digitized projection data. In some embodiments, the image reconstruction module 50 stores the reconstructed image in a storage device or a mass memory 46. Or, the image reconstruction module 50 transmits the reconstructed image to a computer 40 to generate information for diagnosing and evaluating patients. For example, a first scout image and a diagnostic section image are generated on the basis of the projection data acquired by the scout scan or the axial scan or the bolt scan or the other scan modes.

Although the image reconstruction module 50 is illustrated as a separate entity in FIG. 13, in some embodiments, the image reconstruction module 50 may form part of the computer 40, or the image reconstruction module 50 may not exist in the system 10, or the computer 40 may perform one or more functions of the image reconstruction module 50. Furthermore, the image reconstruction module 50 may be located at a local or remote location and may be connected to the system 10 using a wired or wireless network. In some embodiments, computing resources centralized by cloud network may be used for the image reconstruction module 50.

In some embodiments, the system 10 further includes the computer 40, wherein data sampled and digitized by the DAS 26 and/or an image obtained via reconstruction by the image reconstruction module 50 is transmitted to a computer or the computer 40 for processing. In some embodiments, the computer 40 stores the data and/or image in a storage device such as a mass memory 46. The mass memory 46 may include a hard disk drive, a floppy disk drive, a CD-read/write (CD-R/W) drive, a digital versatile disc (DVD) drive, a flash drive, and/or a solid-state storage apparatus. The processor in the computer 40 determines a predicted section image according to the first scout image.

In some embodiments, the computer 40 transmits the reconstructed image and/or other information to a display 42, the display 42 being communicatively connected to the computer 40 and/or the image reconstruction module 50. In some embodiments, the computer 40 may be connected to a local or remote display, printer, workstation and/or similar apparatus, e.g., the computer 40 may be connected to apparatuses of medical institutions or hospitals, or connected to a remote apparatus by means of one or a plurality of configured wires or a wireless network such as the Internet and/or a virtual private network. For example, the display displays the predicted section image and corresponding scanning parameters.

Furthermore, the computer 40 may provide commands and parameters to the DAS 26 and the control mechanism 30 (including the rack controller 32, the X-ray controller 34, and the transport table controller 36), etc. on the basis of user provision and/or system definition, so as to control system operations such as data acquisition and/or processing. In some embodiments, the computer 40 controls system operations on the basis of user input. For example, the computer 40 may receive user inputs, such as commands, scanning protocols and/or scanning parameters, by means of an operator console 48 connected thereto. The operator console 48 may include a keyboard (not shown) and/or touch screen to allow a user to input/select commands, scanning protocols and/or scanning parameters.

In some embodiments, the system 10 may include or be connected to a picture archiving and communication system (PACS) (not shown in the figure). In some embodiments, the PACS is further connected to a remote system such as a radiology information system, a hospital information system, and/or an internal or external network (not shown) to allow operators at different locations to provide commands and parameters and/or access image data.

The method or process described in the aforementioned embodiments may be stored as executable instructions in a non-volatile memory in a computing device of the system 10. For example, the computer 40 may include executable instructions in the non-volatile memory and may apply the medical image processing method in the embodiments of the present application.

The computer 40 may be configured and/or arranged for use in different manners. For example, in some implementations, a single computer 40 may be used; in other implementations, a plurality of computers 40 are configured to work together (e.g., on the basis of distributed processing configuration) or work separately, wherein each computer 40 is configured to handle specific aspects and/or functions, and/or process data for generating models used only for a specific system 10. In some implementations, the computer 40 may be local (e.g., in the same place as one or more systems 10, such as in the same facility and/or the same local network); in other implementations, the computer 40 may be remote and thus can only be accessed via a remote connection (e.g., via the Internet or other available remote access technologies). In a specific implementation, the computer 40 may be configured in a manner similar to that of cloud technology, and may be accessed and/or used in a manner substantially similar to that of accessing and using other cloud-based systems.

Once data (e.g., a trained neural network model) is generated and/or configured, the data can be replicated and/or loaded into the medical system 10 in different manners. For example, models may be loaded by means of a directional connection or link between the system 10 and the computer 40. In this regard, communication between different elements may be accomplished by using an available wired and/or wireless connection and/or according to any suitable communication (and/or network) standard or protocol. Alternatively or additionally, the data may be indirectly loaded into the system 10. For example, the data may be stored in a suitable machine-readable medium (e.g., a flash memory card, etc.), and then the medium is used to load the data into the system 10 (e.g., onsite by a user of the system or authorized personnel); or the data may be downloaded to an electronic device (such as a notebook computer, etc.) capable of local communication, and then the device is used onsite (e.g., by a user of the system or authorized personnel) to upload the data to the system 10 by means of a direct connection (e.g., a USB connector, etc.).

Further provided in the embodiments of the present application is a computer-readable program, wherein upon execution of the program, the program causes a computer to perform the medical image processing method described in the aforementioned embodiments in the apparatus, or system, or computer device.

Further provided in the embodiments of the present application is a storage medium storing a computer-readable program, wherein the computer-readable program causes a computer to perform the medical image processing method described in the aforementioned embodiments in the apparatus, or system, or computer device.

The above embodiments merely provide illustrative descriptions of the embodiments of the present application. However, the present application is not limited thereto, and appropriate variations may be made on the basis of the above embodiments. For example, each of the above embodiments may be used independently, or one or more among the above embodiments may be combined.

The present application is described above with reference to specific embodiments. However, it should be clear to those skilled in the art that the foregoing description is merely illustrative and is not intended to limit the scope of protection of the present application. Various variations and modifications may be made by those skilled in the art according to the spirit and principle of the present application, and said variations and modifications also fall within the scope of the present application.

Preferred embodiments of the present application are described above with reference to the accompanying drawings. Many features and advantages of the implementations are clear according to the detailed description, and therefore the appended claims are intended to cover all the features and advantages that fall within the true spirit and scope of said implementations. In addition, as many modifications and variations could be easily conceived of by those skilled in the art, the embodiments of the present application are not limited to the illustrated and described precise structures and operations, but can encompass all appropriate modifications, variations, and equivalents that fall within the scope of the implementations.

The invention claimed is:

1. A medical image processing method, characterized by comprising:

acquiring a first scout image obtained after a scout scan is performed on a subject to be examined;

determining a correspondence between a scout image and a section image on the basis of a deep learning algorithm or a machine learning algorithm;

acquiring training data, the training data comprising training input data and training output data, the training input data comprising a scout image obtained by performing a scout scan in advance on a subject under examination, and the training output data comprising a section image obtained by performing an axial scan or a spiral scan on a region of interest of the subject under examination or an index identifier of the section image;

using the training data to train a neural network model so as to obtain the correspondence;

determining, according to a preset correspondence between a scout image and a section image, a predicted section image corresponding to a first region of interest in the first scout image; and displaying the predicted section image and scanning parameters corresponding to the predicted section image.

2. The method according to claim 1, further comprising:

updating the predicted section image according to adjusted scanning parameters and/or according to an adjusted first region of interest, and displaying in real time the updated predicted section image and scanning parameters corresponding to the updated predicted section image.

3. The method according to claim 2, further comprising:

determining scanning parameters for clinical use according to the updated predicted section image and the scanning parameters corresponding to the updated predicted section image, and using the scanning parameters for clinical use to perform an axial scan or a spiral scan on the subject to be examined so as to obtain a diagnostic section image.

4. The method according to claim 1, wherein the first scout image comprises a normal scout image or a lateral scout image.

5. The method according to claim 1, wherein the scanning parameters comprise at least one of a noise index, a scan tube current and a scanning voltage.

6. The method according to claim 1, wherein the step of determining, according to the preset correspondence between the scout image and the section image, a predicted section image corresponding to the first region of interest in the first scout image comprises:

inputting an image of the first region of interest of the first scout image into the trained neural network model to obtain the predicted section image.

7. The method according to claim 1, wherein subject-under-examination features and/or regions of interest which correspond to different training input data are different; and subject-under-examination features and/or regions of interest and/or scanning parameters which correspond to different training output data are different.

8. The method according to claim 1, wherein the step of determining, according to the preset correspondence between the scout image and the section image, a predicted section image corresponding to the first region of interest in the first scout image comprises:

finding, in the correspondence, candidate scout images corresponding to subjects under examination matching a subject-under-examination feature of the subject to be examined;

comparing the first scout image to the candidate scout images, and selecting a second scout image matching the first scout image from among the candidate scout images; and using a section image in the correspondence that corresponds to a first region of interest of the second scout image as the predicted section image.

9. The method according to claim 8, wherein the subject-under-examination features comprise at least one of: body size, sex and age.

10. A medical image processing apparatus, characterized by comprising:

an acquisition unit, which acquires a first scout image obtained after a scout scan is performed on a subject to be examined;

a first determination unit, which determines, according to a preset correspondence between a scout image and a section image, a predicted section image corresponding to a first region of interest in the first scout image; and a display unit, which displays the predicted section image and scanning parameters corresponding to the predicted section image a third determination unit, which determines the correspondence on the basis of a deep learning algorithm or a machine learning algorithm an acquisition module, which acquires training data, the training data comprising training input data and training output data, the training input data comprising a scout image obtained by performing a scout scan in advance on a subject under examination, and the training output data comprising a section image obtained by performing an axial scan or a spiral scan on a region of interest of the subject under examination or an index identifier of the section image; and a training module, which uses the training data to train a neural network model so as to obtain the correspondence.

11. The apparatus according to claim 10, further comprising:

an update unit, which updates the predicted section image according to adjusted scanning parameters and/or according to an adjusted first region of interest, wherein the display unit displays in real time the updated predicted section image and scanning parameters corresponding to the updated predicted section image.

12. The apparatus according to claim 11, further comprising:

a second determination unit, which determines scanning parameters for clinical use according to the updated predicted section image and the scanning parameters corresponding to the updated predicted section image, and uses the scanning parameters for clinical use to perform an axial scan or a spiral scan on the subject to be examined so as to obtain a diagnostic section image.

13. The apparatus according to claim 12, wherein the first determination unit inputs an image of the first region of interest of the first scout image into the trained neural network model to obtain the predicted section image.

14. The apparatus according to claim 10, wherein the first determination unit comprises:

a lookup module, which finds, in the correspondence, candidate scout images corresponding to subjects under examination matching a subject-under-examination feature of the subject to be examined;

a selection module, which compares the first scout image to the candidate scout images, and selects a second scout image matching the first scout image from among the candidate scout images; and a determination module, which uses a section image in the correspondence that corresponds to a first region of interest of the second scout image as the predicted section image.

15. A medical image processing system, characterized by comprising:

a scan device, configured to perform a scout scan on a subject to be examined so as to obtain a first scout image;

a processor, which determines, according to a preset correspondence between a scout image and a section image, a predicted section image corresponding to a first region of interest in the first scout image, wherein the processor is configured to determine, on the basis of a deep learning algorithm or a machine learning algorithm, a correspondence between a scout image and a section image by acquiring training data comprising training input data and training output data, the training input data comprising a scout image obtained by performing a scout scan in advance on a subject under examination, and the training output data comprising a section image obtained by performing an axial scan or a spiral scan on a region of interest of the subject under examination or an index identifier of the section image, and using the training data to train a neural network model so as to obtain the correspondence, and further configured to determine, according to the correspondence, a predicted section image corresponding to a first region of interest in the first scout image; and a display, which displays the predicted section image and scanning parameters corresponding to the predicted section image.

* * * * *